(12) United States Patent
Ota et al.

(10) Patent No.: US 6,593,501 B2
(45) Date of Patent: Jul. 15, 2003

(54) PROCESS FOR THE PREPARATION OF 2,6-XYLENOL

(75) Inventors: Hitoshi Ota, Yokohama (JP); Masaru Aga, Yokohama (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 09/948,787

(22) Filed: Sep. 10, 2001

(65) Prior Publication Data

US 2002/0058848 A1 May 16, 2002

(30) Foreign Application Priority Data

Sep. 18, 2000 (JP) ........................................ 2000-281126

(51) Int. Cl.⁷ ............................................... C07C 37/00
(52) U.S. Cl. ....................................................... 568/804
(58) Field of Search ................................. 568/790, 791, 568/794, 804

(56) References Cited

U.S. PATENT DOCUMENTS

| | | | |
|---|---|---|---|
| 3,855,318 A | * | 12/1974 | Nakajima |
| 3,959,394 A | | 5/1976 | Tasaka et al. |
| 3,972,836 A | | 8/1976 | Van Sorge |
| 4,097,411 A | | 6/1978 | van Sorge |
| 4,322,566 A | * | 3/1982 | Leach |
| 4,400,557 A | * | 8/1983 | Fremery |
| 4,418,224 A | | 11/1983 | Bennett et al. |
| 4,503,272 A | | 3/1985 | Bennett, Jr. et al. |
| 4,517,389 A | * | 5/1985 | Katsumata |
| 4,554,388 A | | 11/1985 | Keim et al. |
| 4,661,638 A | | 4/1987 | Battista et al. |
| 4,677,089 A | * | 6/1987 | Bennett |
| 4,900,708 A | | 2/1990 | Bennett et al. |

FOREIGN PATENT DOCUMENTS

| | | |
|---|---|---|
| DE | 3048349 A1 | 7/1982 |
| EP | 0146111 | 6/1985 |
| EP | 0 150 311 A1 | 8/1985 |
| GB | 1253543 | 11/1971 |
| GB | 1289973 | 9/1972 |

OTHER PUBLICATIONS

Abstract of JP–A–05286880 (1993).
Abstract of JP–A–05097739 (1993).

* cited by examiner

Primary Examiner—Michael L. Shippen
(74) Attorney, Agent, or Firm—Birch, Stewart, Kolasch & Birch, LLP

(57) ABSTRACT

A process for producing an aromatic hydroxyl compound alkylated at the ortho position in high yield by subjecting an aromatic hydroxyl compound and an alkyl alcohol to a gas phase catalytic reaction in the presence of a metal oxide catalyst. The aromatic hydroxyl compound is a mixture of a phenol and ortho cresol, and the amount of ortho cresol in the mixture is 0.6 mole or less per 1 mole of phenol.

6 Claims, 1 Drawing Sheet

PROCESS FOR THE PREPARATION OF 2,6-XYLENOL

BACKGROUND OF THE INVENTION

The present invention relates to a novel and advantageous process for producing aromatic hydroxyl compounds alkylated at the ortho position (hereinafter referred to as ortho-position-alkylated aromatic hydroxyl compounds).

The ortho-position-alkylated aromatic hydroxyl compounds (for example, ortho-position-alkylated phenols) are useful as plastic materials, and a number of techniques have long been known regarding their preparation method.

Catalysts comprising iron, vanadium, manganese, magnesium or the like as the main component used in the preparation of these ortho-position-alkylated aromatic hydroxyl compounds are known. For instance, a method using magnesium oxide as catalyst has been proposed (U.S. Pat. No. 3,446,856), but this method suffers from the disadvantage of being difficult to alkylate the ortho position only because of the formation of abundant by-products, that is, ortho position selectivity is low, resulting in a low yield of the objective compound.

As a solution to this problem, use of a catalyst containing vanadium oxide and iron oxide has been proposed (JP-B-47-37943). This catalyst has high activity and allows reactions to proceed relatively low temperature (300–400° C.). The catalyst also produces relatively high ortho-position selectivity. However, this catalyst still fails to provide sufficient ortho-position selectivity for the industrial process to be practicable.

Further, both of the above-mentioned methods suffer the drawback that the alkyl alcohol (such as methanol) used in the reaction tends to decompose during the reaction, generating gases such as $CO_2$, $CO$, $CH_4$ and $H_2$ in abundance. This causes a reduction in the amount of alkyl alcohol available for reaction with the ortho-position of the aromatic hydroxyl compounds.

U.S. Pat. No. 4,097,411 discloses the recovery of unreacted aromatic hydroxyl compounds, which do not take part in the reaction in the production of the ortho-position-alkylated aromatic hydroxyl compounds, and recycling of the recovered compounds for reuse as starting material. This application, however, is silent on the removal of low-boiling point impurities from the recovered aromatic hydroxyl compounds.

SUMMARY OF THE INVENTION

The present invention is designed to provide a process for producing an ortho-position-alkylated aromatic hydroxyl compound in high yield by alkylating the ortho position of an aromatic hydroxyl compound with high selectivity, and also increasing the amount of alkyl alcohol, which is reactable with the ortho position of the aromatic hydroxyl compound.

Thus, the present invention pertains to a process for producing an ortho-position-alkylated aromatic hydroxyl compound by subjecting an aromatic hydroxyl compound and an alkyl alcohol to a gas phase catalytic reaction in the presence of a metal oxide catalyst, said aromatic hydroxyl compound being a mixture of a phenol and ortho cresol, and the amount of ortho cresol in the mixture being 0.6 mole or less per 1 mole of phenol.

Figure 1:
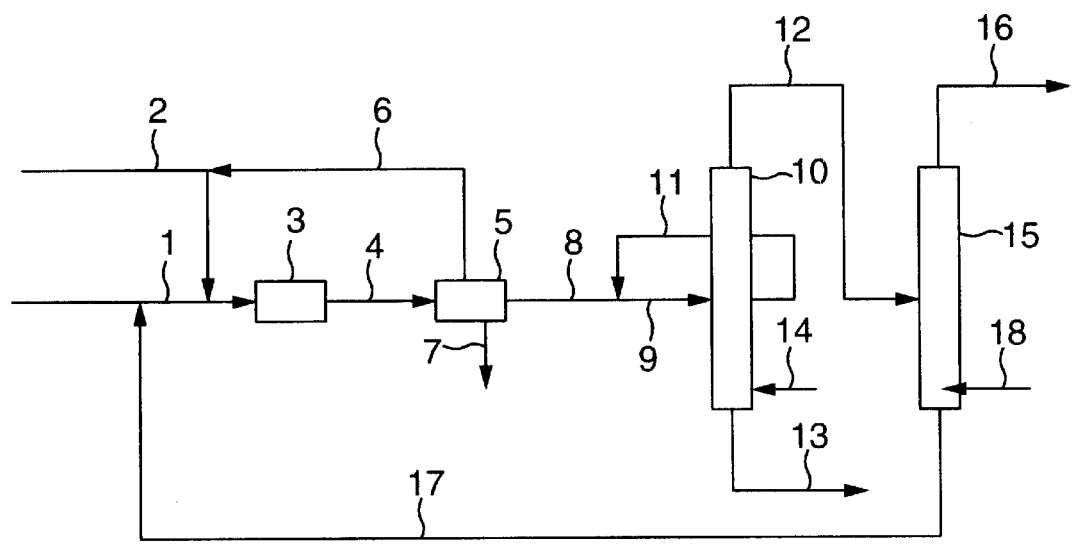
FIG. 1 is a flow sheet of one example of the process according to the present invention.
Figure 2:
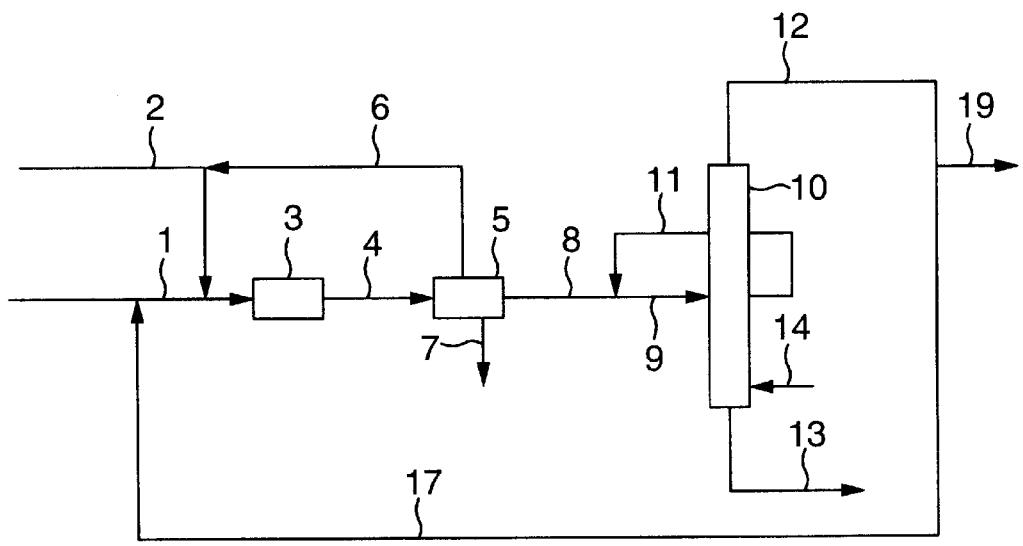
FIG. 2 is a flow sheet of another example of the process according to the present invention.

The reference numerals in FIGS. 1 and 2 designate the following:

1, 2, 4, 6, 7, 8, 9, 12, 13, 14, 16, 17, 18, 19: lines;
3: reactor;
5: preliminary distillation column;
10: first distillation column;
11: side cut;
15: second distillation column.

DETAILED DESCRIPTION OF THE INVENTION

The present invention is described in detail below.
<Starting Materials>

In the preparation of ortho-position-alkylated aromatic hydroxyl compounds according to the present invention, an aromatic hydroxyl compound and an alkyl alcohol are used as starting materials.

The "aromatic hydroxyl compound" used in the present invention is a mixture of a phenol and ortho cresol, in which the amount of ortho cresol is 0.6 mole or less per 1 mole of phenol. By defining the amount of ortho cresol within the above range, it is possible to minimize the formation of by-products during the reaction and to suppress the decomposition of alkyl alcohol. Accordingly, in the preparation of ortho-position-alkylated aromatic hydroxyl compounds according to the present invention, because the formation of by-products can be lessened, it is possible to elevate ortho position selectivity by the alkyl alcohol and to raise the ratio of the portion of the aromatic hydroxyl compound which has been alkylated solely at the ortho position to the supplied aromatic hydroxyl compound. Also, because the alkyl alcohol is less liable to decomposition, it is possible to elevate the ratio of alkyl alcohol which reacts with the ortho position of the aromatic hydroxyl compound relative to the supplied alkyl alcohol. Further, in the present invention, the amount of ortho cresol in the mixture is preferably selected to be 0.25 to 0.5 mole, more preferably 0.3 to 0.4 mole, per 1 mole of phenol.

In the process of the present invention, fresh phenol and ortho cresol or recycled phenol and ortho cresol or a mixture thereof may be used.

The alkyl alcohol used in the present invention is preferably one having 1 to 24 carbon atoms in the molecule. Among such alkyl alcohols, methanol, ethanol and propyl alcohol are more preferred, methanol being especially preferred. Like the above phenol and ortho cresol, fresh alkyl alcohol or recycled alkyl alcohol or a mixture thereof may be used in the process of the present invention.

In the method of alkylating the ortho position of an aromatic hydroxyl compound by the gas phase catalytic reaction of the present invention, the molar ratio of aromatic hydroxyl compound to alkyl alcohol in the feed is preferably selected to be 1:1–20, more preferably 1:2–8.

In the gas phase catalytic reaction of the present invention, steam or an inert gas may be introduced as desired.

The reaction temperature in the gas phase catalytic reaction is preferably set to fall within the range of 250 to 500° C., more preferably 280 to 400° C. The reaction can be conducted under normal pressure, but if necessary, it may be carried out under reduced pressure or under pressure. The gas and catalyst contact time is preferably 0.5 to 50 seconds, more preferably 1 to 20 seconds.

<Catalyst>

The metal oxide catalyst used in the present invention is preferably one which contains at least one metal oxide having a metal selected from the group consisting of iron, vanadium, manganese, magnesium, indium and silica. More preferably, the metal oxide catalyst is one which contains at least one metal oxide having a metal selected from the group consisting of iron, vanadium, indium and silica. Besides the above metals, it is also possible to add other metals including alkaline metals, alkaline earth metals and rare earth metals.

The catalyst may be used together with a suitable carrier such as alumina, silica, silica-alumina, diatomaceous earth, etc., as for instance, described in JP-A-59-65032. The carrier may or may not necessarily be used.

The catalyst can be prepared by various methods. For instance, it can be prepared by a mixing method, impregnation method, precipitation method and the like by using an oxide, ammonium salt, chloride, oxychloride, etc., of vanadium, or an oxide, nitride, chloride, sulfate, oxalate, etc., of iron.

<Production Process>

An example of a production method according to the present invention is illustrated with reference to FIG. 1.

First, an aromatic hydroxyl compound used as starting material, which may be mixed with the unreacted aromatic hydroxyl compound recovered from the bottom of second distillation column 15 to be described later, is supplied to reactor 3 following line 1. Another starting material alkyl alcohol is also supplied to reactor 3 following line 2. This alkyl alcohol may be led into reactor 3 following line 2 after it has been mixed with the unreacted alkyl alcohol and water recovered from the top of preliminary distillation column 5 to be described later.

In reactor 3, the supplied aromatic hydroxyl compound and alkyl alcohol are subjected to a gas phase catalytic reaction in the presence of a metal oxide catalyst to alkylate the ortho position of the aromatic hydroxyl compound. The reactor may be either a fluidized bed type or a fixed bed type reactor. As a result of the gas phase catalytic reaction in reactor 3, there can be obtained an ortho-position-alkylated aromatic hydroxyl compound in the form of a mixture further containing low-boiling point impurities, high-boiling point by-products, unreacted alkyl alcohol, water and unreacted aromatic hydroxyl compound.

In case that it is necessary to remove the high-boiling point by-products, unreacted alkyl alcohol and water before recovering the ortho-position-alkylated aromatic hydroxyl compound, the obtained reaction mixture is supplied to preliminary distillation column 5 following line 4. The unreacted alcohol and water are then recovered from the top of preliminary distillation column 5 and passed through line 6 to be mixed with the starting alkyl alcohol. During this operation, the high-boiling point by-products may be removed from the bottom of the preliminary distillation column 5 and discharged out through line 7.

Then, the mixture containing the ortho-position-alkylated aromatic hydroxyl compound, low-boiling point impurities and unreacted aromatic hydroxyl compound is recovered from preliminary distillation column 5 and supplied to first distillation column 10 through lines 8 and 9. The mixture from preliminary distillation column 5 may be mixed with the distillate from a side cut 11 of first distillation column 10 and supplied to said column 10 through line 9. The mixture from preliminary distillation column 5 and the distillate from side cut 11 may be supplied separately into distillation column 10.

A heat source (steam or heating medium) is supplied to a reboiler(s) at the bottom and/or the side of first distillation column 10 through line 14.

The mixture is supplied to first distillation column 10, and the ortho-position-alkylated aromatic hydroxyl compound is recovered from the bottom of the column while the low-boiling point impurities and unreacted aromatic hydroxyl compound are recovered from the column top.

The ortho-position-alkylated aromatic hydroxyl compound from the bottom of the first distillation column 10 is substantially free of impurities and is of high purity, and it is recovered through line 13.

Then, the low-boiling point impurities and unreacted aromatic hydroxyl compound recovered from the top of the first distillation column 10 are supplied to a second distillation column 15 through line 12. The low-boiling point impurities are then removed from the column top through line 16 while the unreacted aromatic hydroxyl compound is recovered from the column bottom.

Similarly to the first distillation column 10, a heat source (steam or heating medium) is also supplied to a reboiler(s) at the bottom and/or the side of the second distillation column 15 through line 18.

The unreacted aromatic hydroxyl compound recovered from the column bottom through line 17 is recycled to be used as starting material. That is, the recovered unreacted aromatic hydroxyl compound is mixed with the aromatic hydroxyl compound that was fed as starting material, and the mixture is supplied to reactor 3 through line 1.

According to the above-described method of the present invention, when purifying and recovering a high-purity ortho-position-alkylated aromatic hydroxyl compound from a mixture of ortho-position-alkylated aromatic hydroxyl compound, low-boiling point impurities and the unreacted aromatic hydroxyl compound, it is possible to lessen the amount of steam used for separating the ortho-position-alkylated aromatic hydroxyl compound in the distillation column, and to minimize the loss of the active ingredient (aromatic hydroxyl compound) extracted with impurities from the top of the second distillation column.

Said preliminary distillation column 5, first distillation column 10 and second distillation column 15 may be of any type, for example a plate column (such as bubble cap column) or a packed column, and they may be operated either under normal pressure or under pressure or reduced pressure. Also, plural distillation columns may be used as the preliminary distillation column, the first distillation column or the second distillation column. It is expedient to provide the feed plate at a position where the composition of the material in the column and the composition of the feed material are the closest to each other.

Side cut 11 in first distillation column 10 is a means for securing stability of the product purity against variation of the feed material composition, and is not essential. The distilling-out opening at the column side is situated within the area from ¼ of the total number of plates on the upper side of the feed plate to ¼ of that on the lower side, preferably coincidental with the feed plate.

Also, any of said preliminary distillation column 5, first distillation column 10 and second distillation column 15 may be of either batch type or continuous operation type, or a combination of both types.

If the operation of the second distillation column is conducted batch-wise, it is not always necessary to provide a second distillation column 15, and a first distillation column 10 may be used again for the distillation of the unreacted aromatic hydroxyl compound and low-boiling point impurities. That is, the unreacted aromatic hydroxyl compound and low-boiling point impurities recovered from the top of first distillation column 10 are stored in a tank and thence supplied to the first distillation column 10 in place of the mixture from preliminary distillation column 5 supplied through line 8, and the low-boiling point impurities are removed from the top of first distillation column 10 while the unreacted aromatic hydroxyl compound is recovered from the bottom of first distillation column 10 and recycled back to the reactor.

As described above, when an ortho-position-alkylated aromatic hydroxyl compound is produced according to the method of the present invention, the reactivity of the aromatic hydroxyl compound is elevated and the ortho position of this compound can be alkylated with high selectivity. Further, it is possible to increase the amount of alkyl alcohol available for reaction at the ortho position of the aromatic hydroxyl compound, making it possible to obtain a desired ortho-position-alkylated aromatic compound.

DESCRIPTION OF PREFERRED EMBODIMENTS

The present invention will be further illustrated by the following examples and comparative examples. For the evaluation of the reaction results in the Examples and the Comparative Examples, there were used the formulae defined below. All the amounts shown in the formulae are by mole unless otherwise noted.

[1] Conversion of aromatic hydroxyl compound: $X$ (%)

$$X = \left(1 - \frac{\text{Amount of unreacted aromatic hydroxyl compound}}{\text{Amount of supplied aromatic hydroxyl compound}}\right) \times 100$$

[2] Ratio of the portion of the aromatic hydroxyl compound which has been alkylated at the ortho position alone to the supplied aromatic hydroxyl compound (ortho position selectivity of aromatic hydroxyl compound): $Y$ (%)

$$Y = \frac{\text{Overall amount of compound alkylated at only the ortho position}}{\text{Amount of supplied aromatic hydroxyl compound}} \times 100$$

[3] Ratio of alkyl alcohol that reacted with the ortho position of aromatic hydroxyl compound to the supplied alkyl alcohol: $Z$ (%)

$$Z = \frac{\text{Amount of alkyl alochol reacted with ortho position of aromatic hydroxyl compound}}{\text{Amount of supplied alkyl alcohol}} \times 100$$

[4] Yield of trialkylphenol $W$ (%)

$$W = \frac{\text{Amount of trialkylphenol formed}}{\text{Amount of supplied aromatic hydroxyl compound}} \times 100$$

EXAMPLES 1–4 AND COMPARATIVE EXAMPLE 1

Ammonium metavanadate ($NH_4VO_3$) was dissolved in pure water heated at 90° C., to which ferric nitrate [$Fe(NO_3)_3 \cdot 9H_2O$] and silica sol (Snowtex N produced by Nissan Chemical Co., Ltd.) containing 30 wt % of $SiO_2$ were added with sufficient stirring. The produced slurry was sent to a parallel flow type spray dryer and dried thereby. The resulting dry powder was subjected to preliminary calcination at 300° C. for 2 hours by a rotary disc type kiln and then calcined at 680° C. for 3 hours to obtain a catalyst.

800 g of this catalyst was supplied to a 2 inch-diameter fluidized bed reactor to which a mixed solution of phenol, ortho cresol, methanol and water (=1:0.05–0.7:3:1.5 by mole) was supplied an evaporator to carry out the reaction for 200 hours. The reaction was controlled so that the feed of phenol per hour per 1 kg unit catalyst weight would become 0.075 kg. The reaction temperature was selected so that the phenol conversion would become roughly 90 or more, while the atmospheric pressure was maintained throughout the reaction.

The whole amount of the effluent gas from the reactor was passed through a condenser, and the gas passed through the condenser and the condensate were analyzed by gas chromatography, obtaining the results shown in Table 1.

EXAMPLES 5–7 AND COMPARATIVE EXAMPLE 2

The same reaction and analysis procedures as in Example 1 were conducted except for use of a mixed solution of phenol, ortho cresol, methanol and water at a molar ratio of 1:0.25–0.7:5:1.5. The results are shown collectively in Table 1.

EXAMPLES 8–10 AND COMPARATIVE EXAMPLE 3

The same reaction and analysis procedures as in Example 1 were conducted except for use of a mixed solution of phenol, ortho cresol, methanol and water at a molar ratio of 1:0.25–0.7:7:1.5. The results are shown collectively in Table 1.

TABLE 1

| | Composition of mixed solution of starting materials (moles) | | | | Alkylating reaction | | Reaction results | | | |
|---|---|---|---|---|---|---|---|---|---|---|
| | Phenol | Ortho cresol | Methanol | Water | Contact time (sec) | Reaction temperature (° C.) | X (%) | Y (%) | Z (%) | W (%) |
| Example 1 | 1 | 0.05 | 3 | 1.5 | 16 | 341 | 98.2 | 96.4 | 57.4 | 1.6 |
| Example 2 | 1 | 0.25 | 3 | 1.5 | 15 | 348 | 95.0 | 93.1 | 59.1 | 1.8 |
| Example 3 | 1 | 0.35 | 3 | 1.5 | 15 | 344 | 93.3 | 91.6 | 57.8 | 1.6 |
| Example 4 | 1 | 0.5 | 3 | 1.5 | 15 | 343 | 90.3 | 88.8 | 55.8 | 1.4 |
| Comp. Example 1 | 1 | 0.7 | 3 | 1.5 | 15 | 337 | 78.0 | 77.1 | 42.4 | 0.9 |
| Example 5 | 1 | 0.25 | 5 | 1.5 | 12 | 334 | 95.3 | 94.0 | 39.8 | 1.2 |
| Example 6 | 1 | 0.35 | 5 | 1.5 | 12 | 333 | 93.5 | 92.3 | 38.6 | 1.1 |
| Example 7 | 1 | 0.5 | 5 | 1.5 | 12 | 332 | 88.6 | 87.6 | 36.8 | 0.9 |
| Comp. Example 2 | 1 | 0.7 | 5 | 1.5 | 12 | 331 | 76.6 | 75.9 | 33.3 | 0.7 |
| Example 8 | 1 | 0.25 | 7 | 1.5 | 9 | 328 | 94.7 | 93.6 | 31.6 | 1.1 |
| Example 9 | 1 | 0.35 | 7 | 1.5 | 9 | 329 | 93.1 | 92.0 | 28.9 | 1.0 |
| Example 10 | 1 | 0.5 | 7 | 1.5 | 9 | 330 | 90.0 | 88.0 | 27.7 | 0.9 |
| Comp. Example 3 | 1 | 0.7 | 7 | 1.5 | 9 | 332 | 81.1 | 80.1 | 18.5 | 0.9 |

It is seen from Table 1 that when the amount of ortho cresol in the mixed solution of starting materials is made 0.6 mole or less per 1 mole of phenol, the ratio of the portion of the aromatic hydroxyl compound which has been alkylated at only the ortho position to the supplied aromatic hydroxyl compound increases, so does the ratio of the alkyl alcohol, which has reacted with the ortho position of the aromatic hydroxyl compound, to the supplied alkyl alcohol.

EXAMPLE 11

From the reaction product obtained in Example 1, unreacted methanol and water were separated and the residual mixed solution was purified according to the process of FIG. 1. The composition of the mixed solution was: 64.3 wt % of 2,6-xylenol, 26.3 wt % of ortho cresol, 6.6 wt % of phenol, 0.3 wt % of anisole, 1.3 wt % of ortho-methylanisole and 1.2 wt % of methylbenzofuran. This solution was supplied to the first distillation column (packed column) (1,880 kg/hr), and a mixture of low-boiling point impurities (anisole, ortho-methylanisole and methylbenzofuran), phenol and ortho cresol was recovered (520 kg/hr) from the column top while 2,6-xylenol with a purity of 99.98 wt % was recovered (930 kg/hr) from the column bottom. During this operation, a mixture of 2,6-xylenol and ortho cresol was distilled out (430 kg/hr) from a column side at the same position with the feed plate. The operating conditions were: column top pressure=340 mmHg; reflux rate=7; amount of steam used= 5.2 ton/hr.

Then the mixture of low-boiling point impurities (anisole, ortho-methylanisole and methylbenzofuran), phenol and ortho cresol was supplied to the second distillation column (packed column), and a mixture comprising low-boiling point impurities containing 12.8 wt % of anisole, 37.4 wt % of ortho-methylanisole and 13.4 wt % of methylbenofuran, 32.1 wt % of phenol and 4.3 wt % of ortho cresol was removed (25 kg/hr) from the column top, while phenol and ortho cresol were recovered (495 kg/hr) from the column bottom and supplied to reactor 3 for recycling as starting materials. The operating conditions were: column top pressure=235 mmHg; reflux rate=20; amount of steam used=0.6 ton/hr. The yield of the active ingredients (phenol and cresol in this case) in the substances removed from the top of the second distillation column was 9 kg/hr.

EXAMPLE 12

The following operation was carried out according to the process of FIG. 2. According to Example 11, distillation of the mixed solution was carried out in the first distillation column, with the distillate from the column top being recycled to the reactor. This operation was continued for a given period of time. The composition of the solution supplied to the first distillation column was: 51.2 wt % of 2,6-xylenol, 25.2 wt % of ortho cresol, 5.7 wt % of phenol, 3.0 wt % of anisole, 10.1 wt % of ortho-methylanisole and 4.8 wt % of methylbenzofuran.

This solution was supplied (2,260 kg/hr) to the first distillation column (packed distillation column), and a mixture comprising the impurities (8.2 wt % of anisole, 25.8 wt % of ortho-methylanisole and 10.0 wt % of methylbenzofuran), 15.0 wt % of phenol and 41.0 wt % of ortho cresol was recovered (810 kg/hr) from the column top. A portion (35 kg/hr) of the distillate was removed, with the remainder being recycled back to the reactor. Meanwhile, 2,6-xylenol with a purity of 99.98 wt % was recovered (930 kg/hr) from the column bottom. During this operation, a mixture of 2,6-xylenol and ortho cresol was also distilled out (520 kg/hr) from a column side at the same position with the feed plate in the first distillation column. The operation conditions were: column top pressure=340 mmHg; reflux rate=7; amount of steam supplied=7.7 ton/hr. The yield of the active ingredients in the substances removed from the top of the first distillation column was 20 kg/hr.

The results of Examples 11 and 12 are shown in Table 2.

TABLE 2

| | Amount of steam used (ton/hr) | | | Loss of active ingredients (kg/hr) | |
|---|---|---|---|---|---|
| | First distillation column | Second distillation column | Total | First distillation column | Second distillation column |
| Example 11 | 5.2 | 0.6 | 6.1 | — | 9 |
| Example 12 | 7.7 | — | 7.7 | 20 | — |

What is claimed is:
1. A process for producing an aromatic hydroxyl compound alkylated at the ortho position, which comprises carrying out a gas phase catalytic reaction of an aromatic hydroxyl compound and an alkyl alcohol in the presence of a metal oxide catalyst and recovering and recycling the unreacted aromatic hydroxyl compound as starting material after the gas phase catalytic reaction, wherein said aromatic hydroxyl compound is a mixture of phenol and ortho cresol, and wherein the reaction mixture obtained from the gas phase catalytic reaction of an aromatic hydroxyl compound and an alkyl alcohol is supplied to a first distillation column, recovering from the column bottom the produced ortho-position-alkylated aromatic hydroxyl compound while recovering from the column top the unreacted aromatic hydroxyl compound and low-boiling point impurities and then the unreacted aromatic hydroxyl compound and low-boiling point impurities are supplied to a second distillation column, recovering from the column bottoms the unreacted aromatic hydroxyl compound and recycling it as starting material.

2. The process according to claim 1, wherein the alkyl alcohol is one having 1 to 24 carbon atoms in the molecule.

3. The process according to claim 1, wherein the reaction temperature in the gas phase catalytic reaction is within the range of 280 to 400° C.

4. The process according to claim 1, wherein the amount of ortho cresol in said mixture of phenol and ortho cresol is 0.6 mole or less per 1 mole of phenol.

5. The process according to claim 1, wherein the amount of ortho cresol in said mixture of phenol and ortho cresol is 0.25 to 0.5 mole per 1 mole of phenol.

6. The process according to claim 1, wherein said metal oxide catalyst contains at least one metal oxide having a metal selected from the group consisting of iron, vanadium, indium and silica.

* * * * *